Feb. 11, 1941. F. H. HOWARD Plant Pat. 450
ROSE PLANT
Filed July 31, 1940
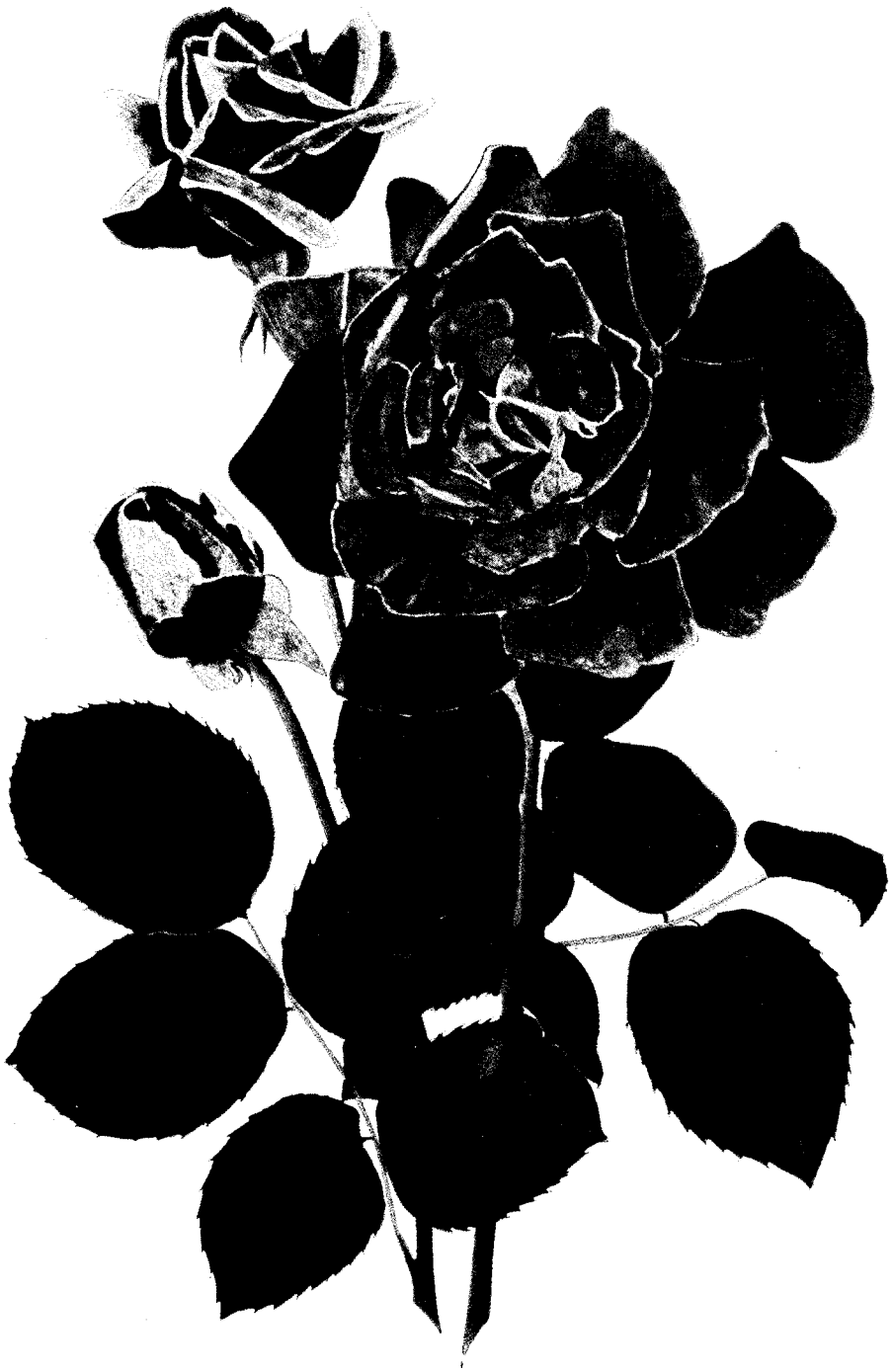
INVENTOR
Frederick Huber Howard
By Orville M. Kile
Plant Patent Agt.

Patented Feb. 11, 1941

Plant Pat. 450

UNITED STATES PATENT OFFICE

450

ROSE PLANT

Frederick Huber Howard, Montebello, Calif.

Application July 31, 1940, Serial No. 348,974

1 Claim. (Cl. 47—61)

My present invention relates to improvements in climbing roses and is the result of a cross made by me of Miss Rowena Thom by Paul's Lemon Pillar.

The flowers of this variety are exceptionally large and perfect for a climbing rose and they are of a brilliant red color which defies description. They are very fragrant and last exceedingly well. With this combination of characteristics they make excellent cut flowers.

The variety has been asexually reproduced and has retained its outstanding characteristics.

The original illustrations accompanying this application show three specimens of this variety in varying stages of maturity and in as nearly their true colors as the artist was able to show them. It must be understood, however, that it was impossible to show the brilliance which is a feature of the color of this rose.

Following is a detailed description of the plant and flower of this rose variety. Color references are to Ridgway's Color Standards and Nomenclature except where the ordinary dictionary term is obviously intended.

*The plant*

Growth: Very vigorous climber, sending out many basal canes. If main shoots are heavily pruned, it makes a bushy plant which is completely covered with bloom.

Blooming habit: Abundant bloomer May to July and October to November.

Foliage: Clean; abundant; spaced close together on stem; compound, usually with five leaflets.

*Leaflets.*—Round to oval; often irregular; relatively broad; finely serrated; acuminate at point; veins prominent; average size, 1½ inches by 1¾ inches.

Stems: Strong; stiff; short-noded; Cerro Green (Plate V), with frequently a reddish tinge.

Rachis: Medium; grooved and tinged red on upper surface; small, sharp thorns on lower surface.

Stipules: Narrow; clinging; points long.

Thorns: Very small; reddish; sharp; hooked downward.

*The flower*

Bud:

*Form.*—Exceptionally well formed; pointed; medium in length.

*Size.*—Medium.

*Color.*—Deep crimson.

*Peduncle.*—Very short; covered with extremely fine spines; tinged with red.

Blossom:

*Borne.*—Frequently borne in clusters of two or three.

*Size.*—Approximately 5 inches in diameter. Large for a climbing rose.

*Form.*—Full; high-centered at first, later opening to cup shape.

*Color.*—Brilliant deep crimson. The nearest designation in Ridgway's is Carmine (Plate I) to Oxblood Red (Plate I), but with a greater brilliance. The reverse of the petals has a little more of the tones of Scarlet Red (Plate I).

*Aspect.*—Rich velvet on inner surface of petals; silky on outer surface.

*Petalage.*—Approximately 30 petals.

*Petals.*—*Size.*—Outer petals 1¾ inches long by approximately the same in width. *Shape.*—Almost round; wavy on edge; cupped.

*Fragrance.*—Strong tea fragrance. Very delightful.

*Longevity.*—Flowers last unusually well.

Reproductive organs:

*Pistils.*—Many; tightly bunched. *Styles.*—very short, tinged with red. *Stigmas.*—Light yellow.

*Stamens.*—Many; surround pistils. *Filaments.*—Much longer than pistils; tinged with red; thin; irregular in length. *Anthers.*—Ochraceous-Buff (Plate XV).

Sepals: Simple.

*Ovaries.*—Large; bright in color.

*Comparison*

The variety known to me which is most like my new variety is Billy Boiler, from which my new variety differs principally as follows:

1. The flowers of my new variety are of a more perfect form.

2. The flowers of my new variety are of a more brilliant red color.

3. The flowers of my variety last longer as cut flowers.

4. My variety has much more intensity of fragrance.

5. My variety probably does not grow quite so tall but sends out a great many more basal canes.

Having thus disclosed my invention, I claim:

A new and distinct variety of climbing hybrid tea rose plant, substantially as shown and described, characterized particularly by its vigorous growth; its habit of producing many basal canes; the perfect formation of its bud; and its abundant production of large, full flowers of excellent cupped form and brilliant deep crimson color which are also intensely fragrant and last exceptionally well as cut flowers.

FREDERICK HUBER HOWARD.